United States Patent [19]

Higo et al.

[11] Patent Number: 5,932,227

[45] Date of Patent: Aug. 3, 1999

[54] PERCUTANEOUSLY ADMINISTRABLE BASE COMPOSITION AND DRUG COMPOSITION PREPARED THEREFROM

[75] Inventors: Naruhito Higo; Yukio Kojima; Ken-ichi Komori, all of Ibaragi, Japan

[73] Assignee: Hisamitsu Pharmaceutical Co., Inc., Saga, Japan

[21] Appl. No.: 08/374,603

[22] PCT Filed: Jul. 23, 1993

[86] PCT No.: PCT/JP93/01034

§ 371 Date: Mar. 29, 1995

§ 102(e) Date: Mar. 29, 1995

[87] PCT Pub. No.: WO94/02119

PCT Pub. Date: Feb. 3, 1994

[30] Foreign Application Priority Data

Jul. 23, 1992 [JP] Japan ..................................... 4-218369
Aug. 4, 1992 [JP] Japan ..................................... 4-229226

[51] Int. Cl.$^6$ ...................................................... A61K 9/08
[52] U.S. Cl. ............................................. 424/401; 424/449
[58] Field of Search ..................................... 424/448, 449, 424/241, 489, 452, 455; 514/772.4

[56] References Cited

U.S. PATENT DOCUMENTS

| | | | |
|---|---|---|---|
| 4,082,881 | 4/1978 | Chen et al. | 424/241 |
| 4,552,872 | 11/1985 | Cooper et al. | 514/175 |
| 5,254,348 | 10/1993 | Hoffmann et al. | 424/449 |
| 5,571,530 | 11/1996 | Nakano et al. | 424/448 |

*Primary Examiner*—Thurman K. Page
*Assistant Examiner*—William E. Benston, Jr.
*Attorney, Agent, or Firm*—Wenderoth, Lind & Ponack, L.L.P

[57] ABSTRACT

A percutaneously administrable base composition which facilitates the percutaneous absorption of drugs and is remarkably reduced in the irritancy against the skin. The composition comprises 10–60 wt. % of lower alcohol, 10–50 wt. % of humectant, 10–70 wt. % of water, 0.1–15 wt. % of abirritant and 0.1–15 wt. % of absorption promoter. A drug composition is prepared by adding to the above composition various active ingredients such as antitussive, expectorant, skeletal muscle relaxant, antivertiginous drug, narcotic, drug for the circulatory system, and so forth.

18 Claims, No Drawings

PERCUTANEOUSLY ADMINISTRABLE BASE COMPOSITION AND DRUG COMPOSITION PREPARED THEREFROM

This application is a 371 of PCT/JP 93/01034 filed Jul. 23, 1993.

FIELD OF THE INVENTION

The present invention relates to a irritation percutaneously administrable base composition which increases percutaneous absorption of a drug and has a low irritation against skin, and a drug composition prepared therefrom.

BACKGROUND OF THE INVENTION

As conventional drug administration method, oral administration, rectal administration, intracutaneous administration, and intravenous administration are generally known. Especially oral administration is popularly adopted among others. Oral administration has been defective in that the liver is susceptible to primary metabolism after absorption of the drug, and a higher blood concentration of drug than the necessary level is observed temporarily after oral administration. Furthermore, many cases of gastrointestinal trouble, feeling of vomiting, anorexia and other side effects are reported.

Recently, therefore, with a view to solving these defects of oral administration, the method of percutaneous administration is attracting the general attention as permitting absorption of a drug safely and continuously. Efforts have been made to develop external-use drugs for this purpose, and some products have already been put to the market.

In the drugs for such percutaneous administration, however, percutaneous absorption of the drug is still on a low level in many cases, and the object seems to be far from fully being achieved.

More particularly, normal skin has originally a barrier function of preventing ingression of an exenobiotic substance into the body. A base alone used for ordinary percutaneous administration cannot therefore ensure sufficient percutaneous absorption of effective ingredients blended therein. It is therefore necessary to make contrivances to improve percutaneous absorption of a drug by controlling the barrier function of the horny substance layer of skin. For this purpose, blending of a material known as percutaneous absorption promoter into the base is generally attempted. For example, there have been proposed dimethyl acetamide combined with ethyl alcohol, isopropyl alcohol or myristyl alcohol as an absorption promoter in combination with a lower alkylamide (U.S. Pat. No. 3,472,931), a combination of 2-pyrrolidone, an appropriate oil, and a straight-chain fatty acid with ester of alcohol (U.S. Pat. No. 4,017,641), and a combination of a lower alcohol having a carbon number of from 7 to 20, an aliphatic hydrocarbon having a carbon number of from 5 to 30, an alcohol ester of aliphatic carboxylic acid having a carbon number of from 19 to 26, mono- or di-ether having a carbon number of from 10 to 24, and ketone having a carbon number of from 11 to 15 with water (Japanese Patent Provisional Publication No. 61-249.934).

However, these conventional absorption promoter and absorption promoting compositions cannot as yet be considered to be sufficient in safety of skin. Percutaneous absorption enhancer composition with low irritation to skin (Japanese Patent Provisional Publication No. 2-115,131) has been proposed. In this case also, irritation is observed on the skin of the portion of administration of a subject particularly sensitive to alcohol.

Under such circumstances, these percutaneous administration methods cannot provide sufficient practical merits for use of a drug, and are not therefore as yet satisfactory in drug stability for pharmaceutical purposes, as absorption and low irritation to skin, and manifestation of drug efficacy.

As the example, tulobuterol is a β-stimulant drug having selectively a bronchiectasis function and is known as a therapeutic drug of bronchial asthma, chronic bronchitis, and dyspnea caused by airway obliteration disease. This is in general orally administered in the form of tablets or dry syrup. Orally administered tulobuterol drug has the problem of such adverse side effects as palpitation, defect of circulatory system like increase in cardiac rate, headache, excitement, defect of psycho-nervous system like giddiness and defect of gastric-intestinal disorder like vomiting, anorexia, and other troubles in the psycho-nervous system, and vomiting, anorexia and other troubles in the gastric system. These side effects are considered to attribute to the temporary increase in the drug concentration in blood after oral administration. Continuity of the function is still insufficient in oral drug, and a paroxysm occurring frequently at peep of dawn cannot sufficiently be coped with. As a measure to overcome these defects, therefore, there is a demand for a drug composition permitting a long endurance of the tulobuterol concentration in blood through percutaneous administration, and for this purpose, an external-use drug for percutaneously administering tulobuterol has been proposed (Japanese Patent Provisional Publication No. 63-10,716). The intent of the patent is to prevent temporary increase in the concentration in blood after administration of the drug by using a cream or patch as new method. For the purpose of promoting percutaneous absorption, there can be cited a method of having a composition comprising a lower alcohol, an alcohol having a carbon number of from 7 to 20 or an aliphatic hydrocarbon having a carbon number of from 5 to 30, and water contain effective ingredients (Japanese Patent Provisional Publication No. 61-249,934). This publication discloses applicability of the composition in the form of ointment, plaster, lotion, adhesive tape impregnated form and gel. A transdermal matrix based on a composition comprising polyisobutylene which is a synthetic rubber and tulobuterol which is an effective ingredient is also proposed (Japanese Patent Provisional Publication No. 4-99,720).

However, these conventional methods and compositions therefore cannot as yet be sufficient in stability of drug absorption and irritation to skin, and drug pharmacological effects.

These circumstances are not limited to above-mentioned case of tulobuterol, but are problems common to various drugs in application.

The present invention was developed to solve the problems in the prior art as described above, and has an object to provide a base composition for percutaneous administration, which increases percutaneous absorption of the drug, and has a low irritation to skin of the portion of administration, and a drug composition for percutaneous administration, using the above composition, excellent in stability.

DISCLOSURE OF THE INVENTION

The present invention provides a percutaneously administrable base composition which comprises from 10 to 60 wt. % of lower alcohol, from 10 to 50 wt. % of humectant from 10 to 70 wt. % of water, from 0.1 to 15 wt. % of abirritant, and from 0.1 to 15 wt. % of absorption promoter.

The present invention provides also a drug composition for percutaneous administration containing a drug blended into the above-mentioned base composition.

More specifically, by administering a drug contained in the above-mentioned base composition comprising lower alcohol, the humectant, water, the abirritant, and the absorption promoter, the drug in efficiently absorbed, and irritation to the administered portion is alleviated.

PREFERRED EMBODIMENTS OF THE INVENTION

The present invention provides a base composition for percutaneous administration as a composition of specific ingredients blended at a specific ratio as described above, and a drug composition using such a base composition. Lower alcohols applicable as one of these ingredients include aliphatic alcohols having a carbon number of from 1 to 5 such as ethanol, propanol, isopropanol, butanol, and isobutanol. Among others, ethanol and isopropanol are preferable. One or more of these lower alcohols may be used. Applicable humectant include aliphatic polyhydric alcohols and sugar alcohol. Examples of one or more preferable alcohols include sorbitol, polyethylene glycol, diglycerol, propylene glycol, butylene glycol, dipropylene glycol, sodium pyrrolidone carboxylate, ethyl carbitol, D-xylitol, glycerine, and hyaluronic acid. Among others, glycerol and polyethylene glycol are preferable. Water should preferably be a buffer solution having a pH of from 6 to 7. As the abirritant, medium- or long-chain fatty acid ester or sorbitol fatty acid ester or a mixture thereof are excellent in irritation reducing effect. Among others, glycerine monooleate, glycerine monolaurate or sorbitan monolaurate, or a mixture thereof is particularly preferable as exhibiting a remarkable irritation alleviating effect.

As the absorption promoter, medium- or long-chain fatty acid, aliphatic alcohol or fatty acid ester is preferable, and one with a carbon number of from 7 to 20 is suitably applicable. Among others, lauril alcohol and myristyl alcohol are suitably applicable as exhibiting a particularly high absorption promoting effect and exerting only limited irritation.

In the present invention, these ingredients are blended at a ratio of from 10 to 60 wt. % of lower alcohol, from 10 to 50 wt. % of humectant, from 10 to 70 wt. % of water, from 0.1 to 15 wt. % of abirritant and from 0.1 to 15 wt. % of absorption promoter, or more preferably, from 10 to 40 wt. %, or further more preferably, from 15 to 30 wt. % of lower alcohol. The water content should more preferably be from 20 to 70 wt. %, or further more preferably, from 30 to 50 wt. %.

The humectant such as glycerine or polyethylene glycol should preferably be in an amount of from 20 to 40 wt. %, for further more preferably, from 20 to 30 wt. %. The content of the abirritant such as glycerine monooleate, glycerine monolaurate, and sorbitan monolaurate should preferably be from 1 to 10 wt. %, or further more preferably, from 3 to 10 wt. %. The absorption promoter such as aliphatic alcohol, fatty acid and ester of fatty acid should preferably be in an amount of from 0.1 to 10 wt. %, for further more preferably, from 0.2 to 5 wt. %.

When the concentration of the lower alcohol, a required ingredient of the base composition, is over 60 wt. %, or 30 wt. %, irritation to the subject skin is observed, and the extent of such stimulus tends to increase with the increase in concentration of the lower alcohol. With a lower alcohol concentration of under 10 wt. %, or under 15 wt. %, no acceleration of skin penetration of the drug blended in the base composition is observed, although irritation to the subject skin is non-existent. A concentration of humectant of over 50 wt. %, or over 30 wt %, tends to cause a decrease in skin penetration of the drug. When the concentration of humectant is under 10 wt. %, or under 20 wt. %, irritation to the subject skin is observed in the drug composition.

While a higher concentration of absorption promoter leads to an increase in skin penetration of the drug, irritation to the skin is observed in a drug composition containing o over 15 wt. %, or over 5 wt. % absorption promoter.

For the abirritant, a concentration of under 0.1 wt. %, or under 3 wt. %, gives no effect, and a concentration of over 15 wt. % permits occurrence of irritation to the subject skin.

For the base composition of the present invention comprising the blend of ingredients described above, the value of pH is adjusted within a range of from 4 to 9, or more preferably, from 4 to 7.5.

Drugs for the pharmaceutical composition for percutaneous administration of the present invention used in the above-mentioned percutaneous administration are not particularly limited only if the drug is capable of being percutaneously absorbed, and include hypnotic and sedative drugs (such as nitrazepam and barbital), antipyretic, and analgesic drugs (such as ketoprofen, indometacin, ketorolac, loxoprofen, and tenidap), excitatory and awaking drugs (such as methamephetamine and bemegride), psychoneurotic drugs (such as meprobamate and imipramine), local anesthetic drugs (such as lidocaine and procaine), muscle relaxant drugs (such as tizanidine, eperisone, and dantrolene), parasympathomimetic-agents (such as carpronium and neostigmine), antiparkinsonic and antihistaminic drugs (such as mequitazine and diphenhydramine), cardiotonics drugs (such as dioxin and aminophylline), antihypertensive drugs (such as nifedipine and alphenorol), antianginal drug (such as nitroglycerin and isosorbide nitrate), vasodilator drugs (such as nicametate and cyclandelate), cerebral vasodilating drugs (such as flunarizine and ibudilast), bronchodilator drugs (such as tranilast and tulobuterol), antivertigo drugs (such as betahystine and difenidol), narcotics (such as buprenorphine, morphine and fentanyl), adrenocortical hormone drugs (such as prednisolone and betamethasone), male hormone drugs (such as testosterone), follicle lutein hormone drugs (such as estradiol and estriol), bactericidal and antiseptic drugs for cuticle, wound protecting drugs, aminoglycoside antibiotics drugs (such as kanamycin), and antifungal drugs (such as miconazole). These drugs may be used singly or in combination of two or more, usually within a range of from 0.001 to 20 wt. %.

Among others, drug composition for percutaneous administration of the present invention include skeletal muscular relaxants (tizanidine), bronchodilator (tulobuterol), antivertigo drug (diphenidol), narcotics (buprenorphine, fentanyl), and cerebral vasodilating drug (ibudilast).

The composition for percutaneous administration of the present invention is suitably administered percutaneously as external-use drugs in any of the forms including lotion, impregnated, gel, gel-cream, cream, liniment, nose drop, and reservoir-type patch. A gelating agent (viscosity agent) may be added ea required to these external-use pharmaceutical drugs. Examples of appropriate gelating agent include carboxyvinyl polymer, soda plyoxylate, hydroxypropylmethylcellulose, hydroxyethylcellulose, hydroxypropylcellulose, methylcellulose, and carboxymethylcellulose.

Furthermore, an ultraviolet-ray absorber, an antioxidizer, a preservative or other additive may be added as required. Applicable ultraviolet-ray absorbers include conventionally known p-amino benzoic acid derivatives, anthranilic acid derivatives, salicylic acid derivatives, coumarin derivatives, aminoacid derivatives, benzotriazol derivatives, tetrazol derivatives, imidazolin derivatives, pyrimidine derivatives, dioxane derivatives, furan derivatives, pyrone derivatives, camphor derivatives, nucleic acid derivatives, allantoin derivatives nicotine derivatives, and [ciconine] or vitamin-6 derivatives. Particularly, benzophenone derivatives such as 2-hydroxy-4-methylbenzophenone derivatives are suitably used. Applicable anti-oxidizers include ascorbic acid, stearic acid, sodium ascorbinate, tocopherol (d-body, 1-body or d1-body of α-tocopherol, β-tocopherol, γ-tocopherol, and δ-tocopherol) and ester derivatives thereof, mordihydroguacetylenic acid, di-butyl-hydroxytoluene, butylhydroxyanisole, tert-butylhydroxynone ester gallate (ethyl, propyl, isoamyl and other esters), and 1-oxo-3-methyl-4-isopropylbenzene.

Applicable preservatives include benzoic acid, sodium benzoate, paraoxy ethyl benzoate, paraoxy propyl benzoate, and paraoxy butyl benzoate.

The drug composition for percutaneous administration of the present invention comprises a solution composition. A drug contained therein therefore efficiently and directly absorbed continuously into circulating blood via skin. It exerts only a very slight irritation to the skin onto which the drug is administered. Drug metabolism caused by the first pass effect often observed in the liver upon oral administration is non-existent, ensuring an enduring effective concentration in blood. It is also possible to expect avoidance of adverse side effects which may occur with a sudden increase in concentration in blood upon oral administration. The pharmaceutical composition for percutaneous administration of the present invention is thus useful particularly as an external-use pharmaceutical agent for percutaneous application.

EXAMPLES

Now, the present invention is described further in detail by means of examples. The symbol % in the description of the examples means weight percentage (wt. %) in all cases.

EXAMPLE 1

A mixture as follows was prepared.

| | |
|---|---|
| Ethanol | 24% |
| Aqueous buffer solution | 43% |
| Glycerine | 25% |
| Lauryl alcohol | 0.5% |
| Glycerine monooleate | 3% |
| Sorbitan monolaurate | 1% |
| Carboxymethylcellulose sodium salt | 3.5% |
| (CMC Na) | |
| Total: | 100% |

Tulobuterol hydrochoride in an amount of 3% was added to, and mixed with, this mixture, and a drug composition for percutaneous administration of the present invention was obtained.

EXAMPLE 2

A mixture as follows was prepared.

| | |
|---|---|
| Ethanol | 24% |
| Aqueous buffer solution | 44.5% |
| Polyethylene glycol 300 | 25% |
| Lauryl alcohol | 0.5% |
| Sorbitan monolaurate | 1% |
| Glycerine monooleate | 3% |
| Hydroxypropylmethylcellulose-4000 | 2% |
| (HPMC) | |
| Total: | 100% |

Fentanyl citrate in an amount of 2% was added to, and mixed with, this mixture, and a drug composition for percutaneous administration of the present invention was obtained.

EXAMPLE 3

A mixture as follows was prepared.

| | |
|---|---|
| Ethanol | 24% |
| Aqueous buffer solution | 44.5% |
| Polyethylene glycol 300 | 25% |
| Lauryl alcohol | 30% |
| Glycerine monolaurate | 3% |
| Sorbitan monolaurate | 1% |
| HPMC 4000 | 2% |
| Total: | 100% |

Alphenorol hydrochloride in an amount of 5% was added to, and mixed with, this mixture, and a drug composition for percutaneous administration of the present invention was obtained.

EXAMPLE 4

A following mixture was prepared.

| | |
|---|---|
| Ethanol | 20% |
| Aqueous buffer solution | 45% |
| Polyethylene glycol 300 | 30% |
| Myristyl alcohol | 1% |
| Glycerine monooleate | 2% |
| HPMC 4000 | 2% |
| Total: | 100% |

Ibudilast in an amount of 5% was added to, and mixed with, this mixtures, and a drug composition for percutaneous administration of the present invention was obtained.

EXAMPLE 5

A following mixture was prepared.

| | |
|---|---|
| Ethanol | 24% |
| Aqueous buffer solution | 46% |
| Polyethylene glycol 300 | 35% |
| Myristyl alcohol | 1% |
| Sorbitan monolaurate | 1% |
| HPMC 4000 | 2% |
| Total: | 100% |

Tulobuterol hydrochloride in an amount of 5% was added to, and mixed with, this mixture, and a drug composition for percutaneous administration of the present invention was obtained.

EXAMPLE 6

A following mixture was prepared.

| | |
|---|---|
| Isopropanol | 40% |
| Aqueous buffer solution | 20% |
| Polyethylene glycol 300 | 35% |
| Myristyl alcohol | 1% |
| Sorbitan monolaurate | 2% |
| HPMC 4000 | 2% |
| Total: | 100% |

Tulobuterol hydrochloride in an amount of 1% was added, and mixed with, this mixture, and a drug composition for percutaneous administration of the present invention was obtained.

EXAMPLE 7

A following mixture was prepared.

| | |
|---|---|
| Ethanol | 10% |
| Aqueous buffer solution | 65% |
| Polyethylene glycol 400 | 20% |
| Lauryl alcohol | 1% |
| Sorbitan monolaurate | 2% |
| HPMC 4000 | 2% |
| Total: | 100% |

Tulobuterol hydrochloride in an amount of 10% was added to, and mixed with, this mixture, and a drug composition for percutaneous administration of the present invention was obtained.

COMPARATIVE EXAMPLE 1

A following mixture was prepared.

| | |
|---|---|
| Ethanol | 49% |
| Aqueous buffer solution | 47% |
| Lauryl alcohol | 1% |
| CMC Na | 3% |
| Total: | 100% |

Fentanyl citrate in an amount of 2% was added to, and mixed with, this mixture, and a comparative drug composition was obtained.

COMPARATIVE EXAMPLE 2

A following mixture was prepared.

| | |
|---|---|
| Ethanol | 40% |
| Aqueous buffer solution | 37% |
| Glycerine monooleate | 10% |
| Glycerine | 10% |
| CMC Na | 3% |
| Total: | 100% |

Ibudilast in an amount of 5% was added to, and mixed with, this mixture, and a comparative composition was obtained.

COMPARATIVE EXAMPLE 3

A following mixture was prepared.

| | |
|---|---|
| Ethanol | 30% |
| Aqueous buffer solution | 47% |
| Glycerine | 20% |
| CMC Na | 3% |
| Total: | 100% |

Alphenorol hydrochloride in an amount of 5% was added to, and mixed with, this mixture, and a comparative composition was obtained.

COMPARATIVE EXAMPLE 4

A following mixture was prepared.

| | |
|---|---|
| Ethanol | 30% |
| Aqueous buffer solution | 42% |
| Myristyl acid | 5% |
| Glycerine | 20% |
| CMC Na | 3% |
| Total: | 100% |

Tobuterol hydrochloride in an amount of 3% was added to, and mixed with, this mixture, and a comparative composition was obtained.

Using these drug compositions obtained in the above-mentioned Examples 1 to 7 and comparative examples 1 to 4, a skin penetration test of drugs in vitro was carried out. A skin irritation test was carried out on these drug compositions. The results of these tests are shown in Table 1.

TABLE 1

| Example No. | Quantity of skin penetration ($\mu g/cm^2/hr$) | Skin irritation index (SI value) |
|---|---|---|
| Example | | |
| 1 | 158.5 | 11 |
| 2 | 210.7 | 13 |
| 3 | 320.5 | 18 |
| 4 | 377.5 | 5 |
| 5 | 119.5 | 3 |
| 6 | 112.2 | 16 |
| 7 | 168.4 | 2 |
| Comparative Example | | |
| 1 | 362.7 | 197 |
| 2 | 500.2 | 83 |
| 3 | 50.2 | 7 |
| 4 | 248.7 | 180 |

(Note 1)
In the skin irritation test, the skin irritation index was determined in accordance with the evaluation criteria shown in Table 2.

TABLE 2

| Evaluation critieria | | |
|---|---|---|
| Evaluation | State | Mark |
| − | No reaction | 0 |
| ± | Slight erythema | 0.5 |
| + | Erythema | 1.0 |

TABLE 2-continued

| | Evaluation critieria | |
|---|---|---|
| Evaluation | State | Mark |
| ++ | Erythema + edema (swelling as a whole) | 2.0 |
| +++ | Erythema + edema + papula or small bulla | 3.0 |

Skin irritation index

=[Sum of higher values of irritation immediately after peeloff or after the lapse of 24 hrs]/[Number of subjects]× 100

EXAMPLE 8

For the base composition for percutaneous administration of the present invention, skin irritation of base composition alone was evaluated with various blending ratios.

| (Example 8-1) | |
|---|---|
| Ethanol | 24% |
| Aqueous buffer solution | 51% |
| Glycerine | 25% |
| Total: | 100% |
| (Example B-2) | |
| Ethanol | 24% |
| Aqueous buffer solution | 51% |
| polyethylene glycol | 25% |
| Total: | 100% |
| (Example 8-3) | |
| Ethanol | 24% |
| Aqueous buffer solution | 46% |
| Glycerine | 25% |
| Lauryl alcohol | 1% |
| Glycerine monooleate | 3% |
| Sorbitan monolaurate | 1% |
| Total: | 100% |

The results of evaluation of skin irritation obtained as above are shown in Table 3.

TABLE 3

| Example | Skin irritation index (SI value) |
|---|---|
| Example 8-1 | 15 |
| Example 8-2 | 14 |
| Example 8-3 | 17 |

Skin irritation was far higher than the above-mentioned results when the content of lower alcohol was over 60 wt. %, when the content of humectant was under 10 wt. %, when the content of absorption promoter was over 15 wt. %, and when the content of abirritant was over 15 wt. %.

For cases where drugs were blended with the base composition, the following Example 9 was compared with the Comparative Examples 5 to 9 to evaluate properties of the compositions of the present invention.

EXAMPLE 9

A mixture as follows was prepared.

| Ethanol | 24% |
|---|---|
| Aqueous buffer solution | 44.5% |
| Polyethylene glycol | 25% |
| Lauryl alcohol | 0.5% |
| Glycerine monooleate | 3% |
| Sorbitan monolaurate | 1% |
| HPMC 4000 | 2% |
| Total | 100% |

Tulobuterol hydrochloride in an amount of 3% was added to, and mixed with, this mixture, and a drug composition for percutaneous administration of the present invention was obtained.

COMPARATIVE EXAMPLE 5

A mixture as follows was prepared.

| Ethanol | 0% |
|---|---|
| Aqueous buffer solution | 68.5% |
| Glycerine | 25% |
| Lauryl alcohol | 0.5% |
| Glycerie monooleate | 3% |
| Sorbitan monolaurate | 1% |
| HPMC 4000 | 2% |
| Total: | 100% |

Tulobuterol hydrochloride in an amount of 3% was added to, and mixed with, this mixture, and a comparative composition was obtained.

COMPARATIVE EXAMPLE 6

A mixture as follows was prepared.

| Ethanol | 60% |
|---|---|
| Aqueous buffer solution | 13.% |
| Glycerine | 20% |
| Lauryl alcohol | 0.5% |
| Glycerine monooleate | 0% |
| Sorbitan monolaurate | 0% |
| HPMC 4000 | 2% |
| Total: | 100% |

Tulobuterol hydrochloride in an amount of 3% was added to, and mixed with, this mixture, and a comparative composition was obtained.

COMPARATIVE EXAMPLE 7

A mixture as follows was prepared.

| Ethanol | 24% |
|---|---|
| Aqueous buffer solution | 48.5% |
| Glycerine | 25% |
| Lauryl alcohol | 0.5% |
| Glycerine monooleate | 0% |
| Sorbitan monolaurate | 0% |
| HPMC 4000 | 2% |
| Total: | 100% |

Tulobuterol hydrochloride in an amount of 3% was added to, and mixed with, this mixture, and a comparative composition was obtained.

COMPARATIVE EXAMPLE 8

A mixture as follows was prepared.

| | |
|---|---|
| Ethanol | 24% |
| Aqueous buffer solution | 13.5% |
| Glycerine | 55% |
| Lauryl alcohol | 0.5% |
| Glycerine monooleate | 3% |
| Sorbitan monolaurate | 1% |
| HPMC 4000 | 2% |
| Total: | 100% |

Tulobuterol hydrochloride in an amount of 3% was added to, and mixed with, this mixture, and a comparative composition was obtained.

COMPARATIVE EXAMPLE 9

A mixture as follows was prepared.

| | |
|---|---|
| Ethanol | 24% |
| Aqueous buffer solution | 60% |
| Glycerine | 10% |
| Lauryl alcohol | 0% |
| Glycerine monooleate | 3% |
| Sorbitan monolaurate | 1% |
| HPMC 4000 | 2% |
| Total: | 100% |

Tulobuterol hydrochloride in an amount of 3% was added to, and mixed with, this mixture, and a comparative composition was obtained.

For the above-mentioned Example 9 and Comparative Examples 5 to 9, results of evaluation of the quantity of skin penetration and skin irritation index are shown in Table 4.

TABLE 4

| Example | Quantity of skin penetration ($\mu g/cm^2 hr$) | Skin irritation index (SI value) |
|---|---|---|
| Example 9 | 170.8 | 12.5 |
| Comp.Ex. 5 | 12.5 | 3.8 |
| Comp.Ex. 6 | 324.2 | 130 |
| Comp.Ex. 7 | 147.1 | 45 |
| Comp.Ex. 8 | 70.7 | 9.2 |
| Comp.Ex. 9 | 258.2 | 47.6 |

EXAMPLE 10

A following mixture was prepared.

| | |
|---|---|
| Ethanol | 24% |
| Aqueous buffer solution | 44.5% |
| Glycerine | 25% |
| Lauryl alcohol | 0.5% |
| Glycerine monoleate | 3% |
| Sorbitan monolaurate | 1% |
| HPMC 4000 | 2% |
| Total: | 100% |

Tizanidine hydrochloride in an amount of 1% was added to, and mixed with, this mixture, and a drug composition for percutaneous administration of the present invention was obtained.

EXAMPLE 11

A mixture as follows was prepared.

| | |
|---|---|
| Ethanol | 24% |
| Aqueous buffer solution | 44.5% |
| Glycerine | 25% |
| Lauryl alcohol | 0.5% |
| Glycerine monoleate | 3% |
| Sorbitan monolaurate | 1% |
| HPMC 4000 | 2% |
| Total: | 100% |

Difenidol in an amount of 1% was added to, and mixed with, this mixture, and a drug composition for percutaneous administration of the present invention was obtained.

EXAMPLE 12

A mixture as follows was prepared.

| | |
|---|---|
| Ethanol | 24% |
| Aqueous buffer solution | 44% |
| Glycerine | 25% |
| Lauryl alcohol | 1% |
| Glycerine monoleate | 3% |
| Sorbitan monolaurate | 1% |
| HPMC 4000 | 2% |
| Total: | 100% |

Bprenorpbine hydrochloride in an amount of 1% was added to, and mixed with, this mixture, and a drug composition for percutaneous administration of the present invention was obtained.

For the drug compositions for percutaneous administration of the present invention of the above-mentioned Examples 10 to 12, the quantity of skin penetration and the skin irritation index were evaluated. As is clear from Table 5 showing the results of evaluation, all these compositions had excellent performance.

TABLE 5

| Example | Quantity of skin penetration ($\mu g/cm^2 hr$) | Skin irritation index (SI value) |
|---|---|---|
| Example 10 | 99.2 | 8 |
| Example 11 | 103.2 | 15 |
| Example 12 | 120.0 | 25 |

EXAMPLE 13

A mixture as follows was prepared.

| | |
|---|---|
| Ethanol | 24% |
| Aqueous buffer solution | 43% |
| Glycerine | 25% |
| Lauryl alcohol | 25% |
| Glycerine monooleate | 3% |
| Sorbitan monolaurate | 1% |
| Carboxymethylcellulose-sodium salt | 3.5% |
| (CMC Na) | |
| Total: | 100% |

Tulobuterol hydrochloride in an amount of 3% was added to, and mixed with, this mixture, and a drug composition for percutaneous administration of the present invention was obtained.

EXAMPLE 14

A mixture as follows was prepared.

| | |
|---|---|
| Ethanol | 24% |
| Aqueous buffer solution | 44.5% |
| Polyethylene glycol | 25% |
| Lauryl alcohol | 0.5% |
| Glycerine monolaurate | 3% |
| Sorbitan monolaurate | 1% |
| Hydroxypropylmethylcellulose 4000 | 2% |
| (HPMC 40000 | |
| Total: | 100% |

Tulobuterol hydrochloride in an amount of 3% was added to, and mixed with, this mixture, and a drug composition for percutaneous administration of the present invention was obtained.

EXAMPLE 15

A mixture as follows was prepared.

| | |
|---|---|
| Ethanol | 24% |
| Aqueous buffer solution | 43.5% |
| Polyethylene glycol 400 | 25% |
| Lauryl alcohol | 0.5% |
| Glycerine monolaurate | 3% |
| Sorbitan monolaurate | 1% |
| HPMC 4000 | 2% |
| Total: | 100% |

Tulobuterol hydrochloride in an amount of 0.5% was added to, and mixed with, this mixture, and a drug composition for percutaneous administration of the present invention was obtained.

EXAMPLE 16

A mixture as follows was prepared.

| | |
|---|---|
| Ethanol | 20% |
| Aqueous buffer solution | 45% |
| Polyethylene glycol 400 | 30% |
| Myristyl alcohol | 1% |
| Glycerine monooleate | 2% |
| HPMC 4000 | 2% |
| Total: | 100% |

Tulobuterol hydrochloride in an amount of 5% was added to, and mixed with, this mixture, and a drug composition for percutaneous administration of the present invention was obtained.

EXAMPLE 17

A mixture as follows was prepared.

| | |
|---|---|
| Ethanol | 24% |
| Aqueous buffer solution | 46% |
| Polyethylene glycol | 25% |
| Myristyl alcohol | 1% |
| Sorbitan monolaurate | 1% |
| HPMC 4000 | 2% |
| Total: | 100% |

Tulobuterol hydrochloride in an amount of 3% was added to, and mixed with, this mixture, and a drug composition for percutaneous administration of the present invention was obtained.

EXAMPLE 18

A mixture as follows was prepared.

| | |
|---|---|
| Isopropanol | 40% |
| Aqueous buffer solution | 20% |
| Polyethylene glycol 400 | 35% |
| Myristyl alcohol | 1% |
| Sorbitan monolaurate | 2% |
| HPMC 4000 | 2% |
| Total: | 100% |

Tulobuterol hydrochloride in an amount of 1% was added to, and mixed with, this mixture, and a drug composition for percutaneous administration of the present invention was obtained.

EXAMPLE 19

A mixture as follows was prepared.

| | |
|---|---|
| Ethanol | 10% |
| Aqueous buffer solution | 65% |
| Polyethylene glycol 400 | 20% |
| Lauryl alcohol | 1% |
| Sorbitan monolaurate | 2% |
| HPMC 4000 | 2% |
| Total: | 100% |

Tulobuterol hydrochloride in an amount of 10% was added to, and mixed with, this mixture, and a drug composition for percutaneous administration of the present invention was obtained.

COMPARATIVE EXAMPLE 10

(refer to Japanese Patent Provisional Publication No. 61-249,934)

A mixture as follows was prepared.

| | |
|---|---|
| Ethanol | 49% |
| Aqueous buffer solution | 47% |
| Lauryl alcohol | 1% |
| CMC Na | 3% |
| Total: | 100% |

Tulobuterol hydrochloride in an amount of 3% was added to, and mixed with, this mixture, and a comparative drug composition was obtained.

COMPARATIVE EXAMPLE 11

(refer to Japanese Patent Provisional Publication No. 2-115,131)

A mixture as follows was prepared.

| | |
|---|---|
| Ethanol | 40% |
| Aqueous buffer solution | 37% |
| Glycerin | 10% |
| Glycerine monooleate | 10% |
| CMC Na | 3% |
| Total | 100% |

Tulobuterol hydrochloride in an amount of 3% was added to, and mixed with, this mixture, and a comparative composition was obtained.

For the drug compositions prepared from the above-mentioned Examples 13 to 19 and Comparative Examples 10 to 11, a skin penetration test of tulobuterol was carried out in vitro with the use of skin extirpated from a hairless mouse, and for the same drug compositions, a human skin irritation test was carried out. The results are shown in Table 6.

TABLE 6

| Example | Quantity of skin penetration ($\mu g/cm^2/hr$) | Skin irritation index (SI value) |
|---|---|---|
| Example | | |
| 13 | 158.8 | 11 |
| 14 | 177.7 | 13 |
| 15 | 98.5 | 18 |
| 16 | 152.6 | 5 |
| 17 | 119.5 | 8 |
| 18 | 112.3 | 16 |
| 19 | 166.4 | 2 |
| Comp.Ex. | | |
| 10 | 362.7 | 197 |
| 11 | 116.5 | 83 |

In the skin irritation test, the skin irritation index was determined in accordance with the evaluation in Table 7.

TABLE 7

| | Evaluation criteria | |
|---|---|---|
| Evaluation | State | Mark |
| − | No reaction | 0 |
| ± | Slight erythema | 0.5 |
| + | Erythema | 1.0 |
| ++ | Erythema + edema (swelling as a whole) | 2.0 |
| +++ | Erythema + edema + papula or small bulla | 3.0 |

Skin irritation index

=[Sum of higher values of irritation immediately after peeloff or after the lapse of 24 hrs]/[Number of subjects]× 100

EXAMPLE 20

A mixture as follows was prepared.

| | |
|---|---|
| Ethanol | 24% |
| Aqueous buffer solution (pH: 6.8) | 44.5% |
| Polyethylene glycol 300 | 25% |
| Lauryl alcohol | 0.5% |
| Glycerine monooleate | 3% |
| Sorbitan monolaurate | 1% |
| HPCM 4000 | 2% |
| Total: | 100% |

Tulobuterol hydrochloride in an amount of 2% was added to, and mixed with, this mixture, and an example composition of the present invention was obtained.

COMPARATIVE EXAMPLE 12

A mixture as follows was prepared.

| | |
|---|---|
| Ethanol | 24% |
| Aqueous buffer solution (pH: 4.0) | 44.5% |
| Polyethylene glycol 300 | 25% |
| Lauryl alcohol | 0.5% |
| Glycerine monooleate | 3% |
| Sorbitan monolaurate | 1% |
| HPCM 4000 | 2% |
| Total: | 100% |

Tulobuterol hydrochloride in an amount of 2% was added to, and mixed with, this mixture, and a comparative composition was obtained.

COMPARATIVE EXAMPLE 13

A mixture as follows was prepared.

| | |
|---|---|
| Ethanol | 24% |
| Aqueous buffer solution (pH: 8.0) | 44.5% |
| Polyethylene glycol 300 | 25% |
| Lauryl alcohol | 0.5% |
| Glycerine monooleate | 3% |
| Sorbitan monolaurate | 1% |
| HPCM 4000 | 2% |
| Total: | 100% |

Tulobuterol hydrochloride in an amount of 2% was added to, and mixed with, this mixture, and a comparative composition was obtained.

For the above-mentioned Example 20 and Comparative Examples 12 to 13, the quantity of skin penetration and the skin irritation index were similarly evaluated. The results are shown in Table 8.

As is clear from Table 8, it is desirable to use a buffer solution having a pH of 6 to 7.

TABLE 8

| Example | Quantity of skin penetration ($\mu g/cm^2/hr$) | Skin irritation index (SI value) |
|---|---|---|
| Example 20 | 147.8 | 12.0 |
| Comp.Ex.12 | 30.0 | 17.0 |
| Comp.Ex.13 | 170.0 | 60.0 |

EXAMPLE 21

For the drug composition for percutaneous administration obtained from the above-mentioned Example 20, the concentration in blood of tulobuterol upon administering to a rat, while comparing with oral administration.

The results were a shown in Table 9. The compositions of the present invention are confirmed from Table 9 to be excellent in stability and absorbing function.

TABLE 9

| Time (hr) | Oral administration (10 mg/kg) | Example 20 |
|---|---|---|
| 0.25 | 227.0 | — |
| 0.5 | 37.7 | 16.76 |
| 1 | 17.1 | 51.80 |
| 2 | 4.3 | 247.26 |
| 4 | 0.8 | 318.66 |
| 6 | 0 | — |
| 8 | 0 | 261.95 |
| 12 | 0 | 194.55 |
| 24 | 0 | 124.42 |
| AUC ($\mu ghr/ml$) | 91.01 | 8064.75 |
| Bioavailability (%) | 5.37 | 78.15 |

AREAS OF INDUSTRIAL APPLICATION

According to the base composition and the drug composition for percutaneous administration of the present invention, it is possible to promote absorption of a drug while reduce skin irritation at the portion of administration, and to cause continuous absorption of the drug directly into circulating blood through skin. An effective concentration in blood is continuously available without suffering from metabolism of the drug in the liver caused by first pass effect upon oral administration. It is also expected to avoid adverse side effects which may be caused by a sudden increase in concentration in blood often observed during oral administration of drug concentration of drug.

For these reasons, the present invention is very useful as a novel pharmaceutical prescription.

What is claimed is:

1. A skin penetrating, low irritant composition, comprising:
   (a) from 10 to 40 wt. % of a lower alcohol,
   (b) from 20 to 40 wt. % of a humectant comprising an aliphatic polyhydric alcohol or a sugar alcohol,
   (c) from 20 to 65 wt. % of water,
   (d) from 1 to 10 wt. % of an abirritant comprising a medium-chain or a long-chain fatty acid ester, or a sorbitol fatty acid ester having a carbon chain with a carbon number of from 7 to 20, or a mixture thereof, and
   (e) from 0.1 to 10 wt. % of an absorption promoter, comprising a medium-chain or long-chain fatty acid, aliphatic alcohol or a fatty acid ester having a carbon chain with a carbon number of from 7 to 20.

2. The composition according to claim 1, wherein said humectant comprises glycerine or polyethylene glycol.

3. The composition according to claim 1, wherein said abirritant comprises glycerine monooleate, glycerine monolaurate, sorbitan monolaurate or a mixture thereof.

4. The composition according to claim 1, wherein said absorption promoter comprises lauryl alcohol or myristyl alcohol.

5. The composition according to claim 1, wherein said lower alcohol comprises ethanol or isopropanol.

6. The composition according to claim 1, wherein said water is a buffer solution and has a pH within a range of from 6 to 7.

7. The composition according to claim 1, wherein said composition has a pH within a range of from 4 to 9.

8. The composition according to claim 1, which further contains a therapeutically effective pharmacological ingredient which is percutaneously administratable.

9. The composition according to claim 1, which further contains a therapeutically effective amount of a bronchodilator which is percutaneously administratable.

10. The composition according to claim 1, which further contains a therapeutically effective amount of tulobuterol or a salt thereof which is percutaneously administratable.

11. The composition according to claim 1, which further contains a therapeutically effective amount of a muscle relaxant which is percutaneously administratable.

12. The composition according to claim 1, which contains a therapeutically effective amount of tizanidine or a salt thereof which is percutaneously administratable.

13. The composition according to claim 1, which contains a therapeutically effective amount of an antivertigo agent which is percutaneously administratable.

14. The composition according to claim 1, which contains a therapeutically effective amount of difenidol or a salt thereof which is percutaneously administratable.

15. The composition according to claim 1, which contains a therapeutically effective amount of a narcotic which is percutaneously administratable.

16. The composition according to claim 1, which contains a therapeutically effective amount of buprenorphine or fentanyl or a salt thereof which is percutaneously administratable.

17. The composition according to claim 1, which contains a therapeutically effective amount of a cerebral vasodilating drug which is percutaneously administratable.

18. The composition according to claim 1, which contains a therapeutically effective amount of ibudilast or a salt thereof which is percutaneously administratable.

* * * * *